United States Patent [19]
Bertin

[11] Patent Number: 5,226,915
[45] Date of Patent: Jul. 13, 1993

[54] FEMORAL PROSTHESIS COMPONENT SYSTEM FOR KNEE REPLACEMENT SURGERY

[76] Inventor: Kim C. Bertin, 1879 Ridgehollow Dr., Bountiful, Utah 84010

[21] Appl. No.: 862,954

[22] Filed: Apr. 3, 1992

[51] Int. Cl.$^5$ .............................................. A61F 2/38
[52] U.S. Cl. ........................................................ 623/20
[58] Field of Search ..................... 623/20, 18, 23, 16, 623/22

[56] References Cited

U.S. PATENT DOCUMENTS

| | | | |
|---|---|---|---|
| 4,731,086 | 3/1988 | Whiteside et al. | 623/20 |
| 4,936,847 | 6/1990 | Manginelli | 623/20 |
| 4,950,298 | 8/1990 | Gustilo | 623/20 |
| 4,985,037 | 1/1991 | Petersen | 623/20 |

FOREIGN PATENT DOCUMENTS

| | | | |
|---|---|---|---|
| 0189253 | 7/1986 | European Pat. Off. | 623/20 |
| 3922294 | 1/1991 | Fed. Rep. of Germany | 623/20 |
| 9014806 | 12/1990 | World Int. Prop. O. | 623/20 |

Primary Examiner—David Isabella
Attorney, Agent, or Firm—Sherman and Shalloway

[57] ABSTRACT

A femoral prosthesis component system particularly for knee revision surgery comprising a set of femoral implant components constructed around a set of geometrical constants which allows resection of the distal femur to be conducted using the intramedullary canal as a reference point and without the requirement of first measuring for a specific implant size. The construction of all the components in the set is based around a constant relationship between the intramedullary shaft and the anterior flange such that the anterior resection is the same regardless of the size of the component used and the distal and posterior resections are standard cuts made based on this relationship and the intramedullary canal reference point. Adjustment of the distal and posterior resections to fit is made with a set of augments having dimensions also based on the standard distal and posterior resection cuts.

15 Claims, 3 Drawing Sheets

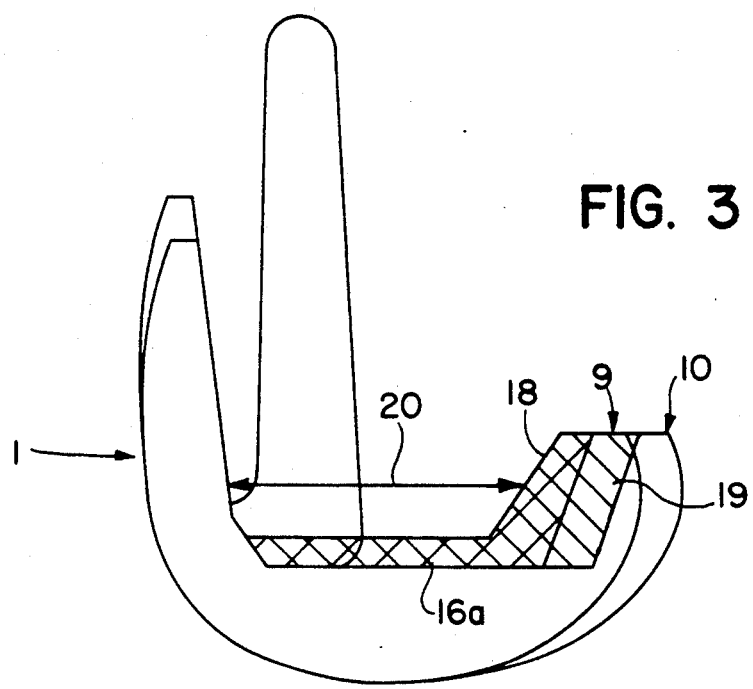
FIG. 3
FIG. 4
| FEMUR SIZE | THICK 1 | THICK 2 | THICK 3 | THIN 1 | THIN 2 | THIN 3 |
|---|---|---|---|---|---|---|
| 1 |   |   |   | A | A | A |
| 2 | A | A | A | B | B | B |
| 3 | B | B | B | C | C | C |
| 4 | C | C | C | D | D | D |
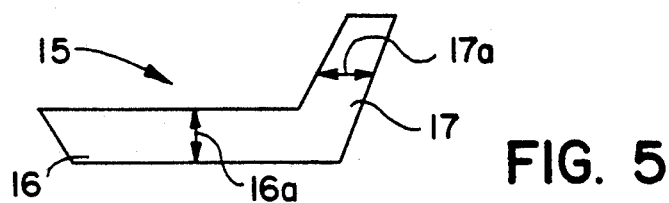
FIG. 5

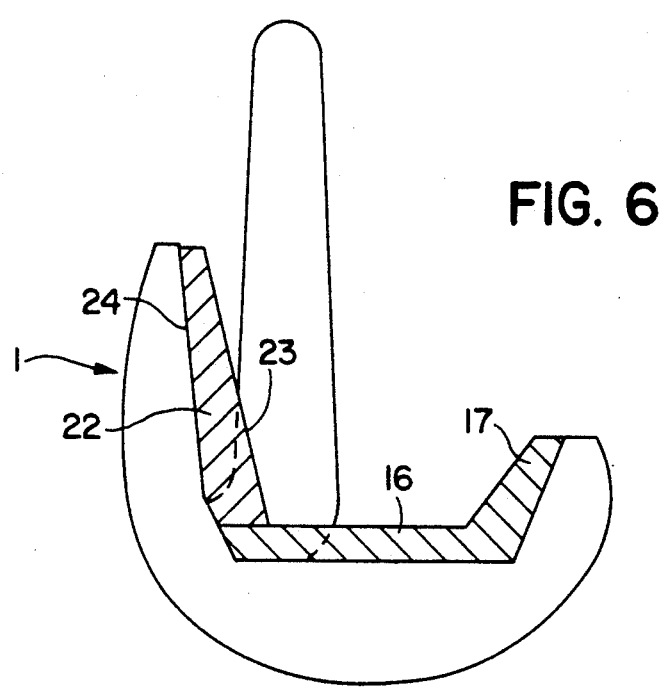
FIG. 6
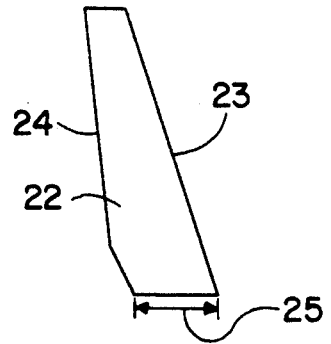
FIG. 7
FIG. 8
| FEMUR SIZE | DISTAL THICKNESS 1 | DISTAL THICKNESS 2 | DISTAL THICKNESS 3 |
|---|---|---|---|
| 1 | E | F | G |
| 2 | E | F | G |
| 3 | E | F | G |
| 4 | E | F | G |

FEMORAL PROSTHESIS COMPONENT SYSTEM FOR KNEE REPLACEMENT SURGERY

FIELD OF THE INVENTION

The present invention relates to a method and apparatus for a knee joint prosthesis and surgical procedure. More particularly, it relates to a system of prostheses for knee revision surgery particularly concerning the femoral component of a total knee revision prosthesis and the method of its use.

BACKGROUND OF THE INVENTION

The present invention relates to a knee prosthesis, surgical procedure and apparatus designed for use as a system in revision surgery of previously performed knee arthroplasties. The prostheses and system of this invention may also find utility in the initial prosthetic replacement of a damaged or diseased knee joint.

Replacement of the femoral and tibial components of knee joints has become more common in recent years as a reconstructive practice for damaged and diseased joints. However, it is still considered that about 10 years is the expected life for prosthetic joint components. Accordingly, it is expected that joint implants will require replacement through a revision procedure.

Revision surgery is performed to correct failures of previously implanted knee prostheses. These failures occur for a number of reasons including malposition, loosening of the prosthesis, infection or dislocation. Such categories are not necessarily mutually exclusive since infection may cause a loosening of the prosthesis which, in turn, might cause dislocation.

When a knee must be replaced or a previously implanted prosthesis removed and a revision prosthesis inserted, it is often the case that additional bone has been removed or lost in the loosening or revision process. When this occurs, the interior portion of the femoral component of the prosthesis must be augmented to add additional thickness to compensate for the bone that has been lost or removed and stabilize the new prosthesis. In addition, the cuts that remove the extra bone must be correctly made relative to the femoral prosthesis, whether an original or revision implant, for accurate positioning in relation to a tibial component and the patella.

If the replacement is done as a staged procedure, there is an opportunity to obtain a mold of the bone ends and to custom manufacture a prosthesis for an accurate fit. Prostheses may also be custom manufactured based on information obtained through X-rays or other imaging systems. However, it is preferable to perform the joint replacement in a single surgical procedure. Furthermore, it is preferable to be able to obtain an optimum functioning knee prostheses for a wide range of patients with as few individual parts as possible. Also, it is desirable to have a system of prostheses constructed around a constant reference point which may be used in initial prosthetic replacement of the knee and in subsequent revision procedures, the constant reference point serving to simplify preparation of the implant site and provide uniformity within the system thereby simplifying the procedures.

DESCRIPTION OF THE PRIOR ART

Prior systems for knee replacement surgery, particularly revision surgery, have involved the above mentioned custom manufacture of prosthesis which is both expensive and time consuming and requires multiple surgical procedures to remove the old prosthesis and accurately measure the femur for preparation of the revision prosthesis, check the fit of the custom device and adjust it if necessary, then finally implant the prosthesis.

Previous prosthesis, such as that of Manginelli, U.S. No. 4,936,847, provide a plurality of augments which are removable and changeable on a trial and error basis for each individual size of prosthesis to accommodate variations in the end of the femur necessitating a wide array of both prostheses and augments. Even with the augments, the procedures employed with these prostheses require measuring and cutting the bone to fit as near as possible the particular size prosthesis. Furthermore, the geometry of each size of a prosthesis in prior systems is particular to that size of implant rather than being based on a constant for all sizes. Such irregularity across the implants of a system introduces a further variable into the procedure of preparation and fitting of a knee revision.

SUMMARY OF THE INVENTION

This invention describes a system of femoral prostheses for knee replacement, particularly revision surgery, which allows bone cuts to be made in the end of the femur without measuring the bone for the size of the individual prosthesis before those cuts are made. Through the use of femoral components constructed around a constant geometry and reference point and augments keyed to resection cuts made in the distal femur, a minimum selection of prostheses need be maintained in stock for use across a wide variety of bone conditions. Furthermore, the cuts may be made from a standardized guide also based on the constant geometry and reference point, such as described by my copending application Serial No. 07/862,953 filed April 13, 1992, thereby assuring compatibility and an accurate fit of the component with both the bone and the soft tissues of the knee.

This invention further provides a method whereby a knee replacement prosthesis may be provided which maintains the correct anatomical structure and operation of a knee joint of a particular size even where the femur has been resected to the point normally associated with a lower size component.

By providing a prosthesis with the construction geometry to be described, one size prosthesis can be used on two or more sizes of femurs with the selection of only two augments instead of maintaining a large array of sizes of prostheses or multiple sizes of augments which must be fit on a trial and error basis. This serves to limit the inventory which must be kept on hand and simplifies the surgical procedure since the constant geometry across the different sizes of implants reduces the amount of test fitting to be done and the surgeon will know better where to make the necessary cuts on the femur and the specific prosthesis and augment combination to use to achieve a correct fit for both the hard and the soft tissues of the knee.

It is therefor an object of this invention to provide a system of femoral knee prostheses having a constant geometry of construction through all sizes of prostheses in the system.

It is a further object to provide a method whereby the prostheses of the system may be used to achieve and maintain the correct anatomical structure and operation of a human knee through revision surgery.

It is a still further object to provide a system of femoral knee prostheses wherein each size of prosthesis in the system has an identical reference point centered on the intramedullary stem of the prosthesis such that the angles thereof are identical for each size of prosthesis in the system.

It is an even further object to provide a system of femoral knee prostheses wherein the relative distance between the intramedullary stem and the anterior flange of each size of prosthesis in the system is identical.

Further objects and advantages will become evident from the following drawing figures and description.

BRIEF DESCRIPTION OF THE DRAWINGS

FIG. 3 is a cross section as in FIG. 2 of two sizes of components according to the system of the present invention illustrating the geometrical constants available across such components with condylar augments in place.

FIG. 4 is a chart illustrating the relationship between the different sizes of femoral revision components, augments and posterior femur resection cuts in the system of the present invention.

FIG. 5 is a cross section of an augment used with the revision component of the present invention illustrating the options available in the system of the present invention.

FIG. 6 is a cross section of a femoral component according to the system of the present invention including an anterior flange augment in combination with distal and posterior flange augments.

FIG. 7 is a cross section of an anterior augment used with the revision component of the present invention illustrating the options available in the system of the present invention.

FIG. 8 is a chart illustrating the relationship between different sizes of femoral revision components, distal augments and anterior augments (E, F and G).

DETAILED DESCRIPTION OF THE INVENTION

Figure 1:
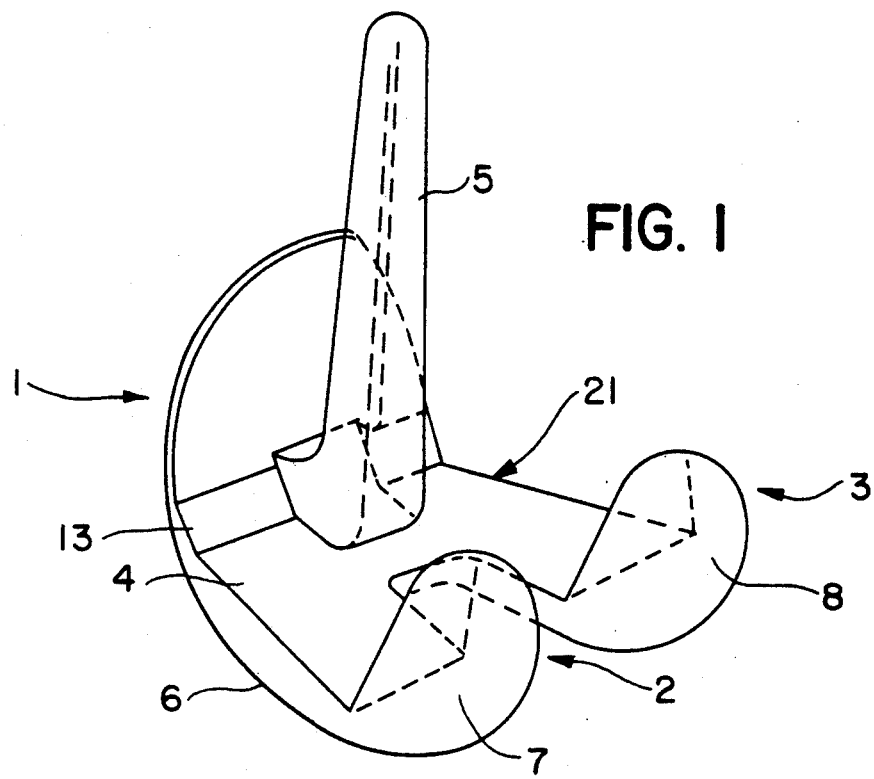
FIG. 1 is an oblique view of a standard femoral component of a knee revision prosthesis as employed in the system of the present invention.

The femoral component revision prosthesis of FIG. 1 is similar to that employed in most knee prosthetics in that it comprises an anterior flange 1, a pair of posterior condylar flanges 2 and 3, a distal femur contacting surface 4, an intramedullary locating and anchor shaft 5 and a distal joint surface 6 corresponding to the natural distal femoral surface of the human knee with condylar surfaces 7 and 8 for cooperation with the corresponding end of a tibia. The relationship of the anterior and posterior flanges 1, 7 and 8 and the distal joint surface 6 is such that an anterior/posterior box 21 is formed bounded on three sides by the femoral contacting surfaces of the flanges and the distal joint surface. The resected distal femur fits into this box 21 with the intramedullary shaft 5 extending into the reamed intramedullary canal of the femur. Means for patellar tracking along the arc of the joint surface of the anterior flange 1 and between the distal condylar surfaces 7 and 8 is also provided. Femoral component prostheses of this general type have been used for some time in knee reconstruction and have been made available in a range of sizes to accommodate patients having different skeletal and joint sizes. Such components have required that the distal end of the femur be resected to the specific size of the individual component, necessitating careful shaving of the bone by the surgeon and multiple fittings of the prosthesis before the procedure is finished. Alternatively, a wide array of augments attachable to the distal femur contacting surface 4 of the component have been necessary to ensure a proper fit of the correct size component to a patient's femur.

For an initial femoral implant, it is generally not as difficult to obtain a correct fit of the proper size component; although the problem can occur where there is a great deal of diseased bone that must be removed before the implant is fitted. Such instances then become similar to those encountered in revision surgery where it is necessary to remove existing bone along with the original implant either due to infection or physical breakdown of the previously prepared distal femur. In these cases the size of the bone supporting the implant is reduced but it is still desired to maintain the size of the original joint in order to obtain proper anatomical characteristics of support and function for the patient. For example, a patient having an original anatomical knee of one size may, following resection of the femur, have a distal femoral surface corresponding to that for a smaller anatomical size knee. In order to maintain the proper anatomical characteristics for that knee, both of the hard and the soft tissues, it is desirable that the implanted component be a size corresponding to that of the original knee. However, adapting a larger size implant to a smaller size bone has presented difficulties which, to date, have been solved by the use of custom made implants, multiple augments, bone grafting or excessive bone cement.

Prior devices and methods have required measuring the size of the bone and then cutting it to fit one specific size of prosthesis. This allows a good fit to be obtained between the prosthesis and the bone but may not provide a good fit with the soft tissues and the patella. Particularly in revision surgery, greater resection of the posterior condyles of the femur often results in the flexion space of the knee being greater than the extension space which then requires additional build up of that area or use of a larger femoral size than the bone measurement would indicate. In other revision prosthesis systems this often means bone grafting or using more bone cement or using custom fabricated implants, all of which have drawbacks including multiple surgical procedures, greater risk of infection or necrosis and subsequent failure of the implant.

The design of the femoral prosthesis system and method of the present invention allows the femoral resection cuts to be made without measuring for the size of the implant prior to making those cuts. Because the implants are constructed around a set of geometric constants, the cuts to be made to the femur may be based on those constants and therefor standardized permitting them to be made first and the proper implant then selected to fit those cuts and provide good results with the soft tissues of the knee.

Figure 2:
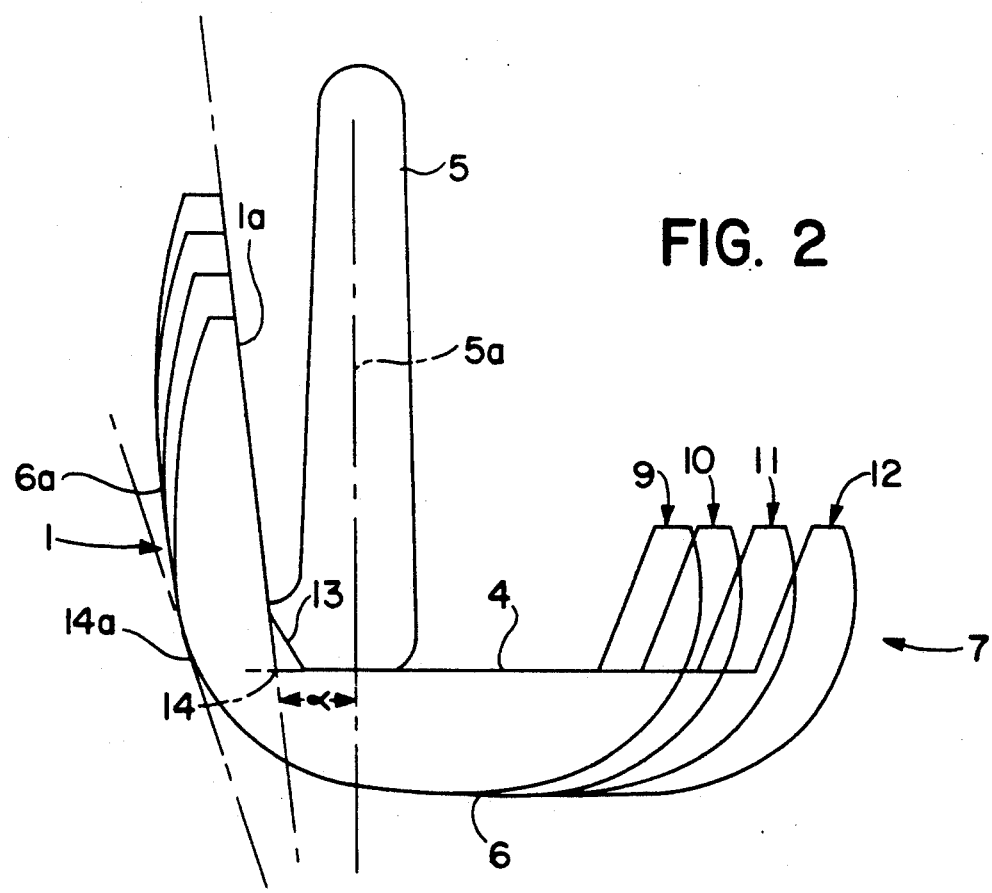
FIG. 2 is a cross section of the femoral component of FIG. 1 illustrating the relationship of different sizes of components available in the system of the present invention and the geometrical constants of their construction.

FIG. 2 illustrates a set of different sizes of implants 9, 10, 11 and 12, employed in the system and their respective relationships. The implants correspond to sequentially increasing sizes which may be arbitrary, but which are preferably based on statistical averages for the human population. As is readily seen in the figure, the sizes increase in the direction of the posterior condylar flanges 7 and 8, represented in this figure by flange 7. However, the relative position of the anterior flange 1 of each implant is identical, the only difference here being in the length of the anterior flange 1. In addition, to maintain the overall anatomical relationships, the width of the prostheses will increase with the size increase, as will the length of the anterior flange 1. Furthermore, the location of the intramedullary shaft 5 relative to the anterior flange 1 is constant across all sizes of implants in the system.

This constancy between the shaft 5 and the anterior flange 1 is based in part on the axis 5a of the shaft 5, which corresponds to the center line of the prepared intramedullary canal, such that the angle alpha between the axis 5a and the inner face 1a of anterior flange 1 along the anterior/posterior axis of the component is the same for each size component 9-12 in the set. To ensure this constancy between implants, the point of measurement for this shaft/flange relationship is the intersection of the planes of inner surface 1a of flange 1 and the distal femur contact surface 4 taken through chamfer 13. That point is designated at 14 in FIG. 2.

An additional constant is the distance between the shaft axis/intramedullary canal center line 5a and the anterior cortex of the femur as represented by the joint surface 6a of the anterior flange 1. This distance is preferably taken at a point corresponding to the transition from the anterior flange joint surface 6a to the distal joint surface 6, designated at 14a in FIG. 2; this point being in line with point 14 along the plane of the distal femur contact surface 4. Alternatively, this constant will be the distance between the shaft axis/intramedullary canal center line 5a and a median point between the tips of the anterior flanges 1 of the smallest and largest implants of a set. Like the sizes of the implants, this point will be based on statistical averages for the human population and will represent the intersection of the inner face 1a of the anterior flange 1 with the anterior cortex of the femur.

In knee replacement surgery, whether primary or revision, it is generally the flexion space between the posterior condylar surfaces of the femur and the proximal tibia which shows the greatest wear and deviation from the norm. The extension space generally exhibits less wear and disruption at the anterior surface is usually negligible. Thus, the areas requiring adjustment to achieve the correct balance of hard and soft tissues and to obtain flexion and extension spaces which are the same, are, in most cases, the posterior and distal joint surfaces. The anterior surface is therefor constant permitting the construction of all the implants of the system with a constant shaft/flange geometry as described. Furthermore, such constant geometry across all of the implants in the system employs the intramedullary space of the femur as a reference point which eliminates a variable in the design and placement of implants thereby providing a constant reference point for determination of the posterior cuts to be made as well as for the fitting of the implants.

The constant geometry of the implants together with the design and size of the augments for use therewith allow the surgeon to choose the appropriate size implant after the posterior and distal cuts are made to the end of the femur. Thus, the surgeon may go up or down in sizes of prostheses as needed after preparing the femur. Furthermore, the system allows the surgeon to easily fit an implant of one size to a bone which has been resected to the point where an implant of a smaller size would normally have to be used. In this manner, the system allows the surgeon to implant a component having the correct anatomical size relative to the soft tissues of the joint, even when necrosis or disease has required resection of the femur a full size or more lower, thereby maintaining the proper working action of the knee. Similarly, as mentioned above, the flexion space between the femur and tibia is often larger than the extension space which usually requires using a larger size femoral implant than would normally be indicated by bone measurements. By providing a constant anterior geometry to all sizes of implants in the system and using the intramedullary canal as a constant point of reference, the distal femur may be resected to predetermined standards by means of cutting guides also using the intramedullary canal as a reference point. Such predetermined resection of the femur also permits the use of a uniform set of augments in combination with the femoral components of the system to establish a correct fit on the bone and with the soft tissues of the knee in order to obtain accurate anatomical function.

As shown in FIG. 4, the augments 15 may have an L-shape and be of one piece construction comprising a distal augment section 16 and a posterior augment section 17. Alternatively, separate distal and posterior augments may be used. No special means for attachment of the augment 15 to the implant is required since there is no trial and error fitting of the implant. Any means for securely attaching the augments to the implant may be used. Preferably, no separate or modular anterior augment is needed since that dimension is constant for all implants in the system. Accordingly, once the cuts are made, the appropriate augments may be selected and cemented or otherwise fixed in place in the implant which is then implanted to the prepared femur.

A variety of augments may be employed but preferably, each femoral component is provided with a series of augments 15 which provide the surgeon with two posterior thicknesses 17a and three distal thicknesses 16a. These thicknesses are selected to correspond to the cuts made to the end of the femur. The posterior thicknesses provide constant anterior/posterior box dimensions across at least two sizes of implants as well as adjustment of flexion space across the knee joint. The distal thicknesses provide adjustment of the extension space across the knee joint so that it can be made to correspond with the flexion space for proper anatomical function of the joint. In this respect, FIG. 3 illustrates a smaller size implant 9 provided with an augment having a thin posterior dimension 18 compared with a larger size implant 10 provided with an augment having a thick posterior dimension 19. In both instances the distal thickness 16a of the augment is the same.

The combination of the constant anterior flange/shaft relationship across the different implants with the fixed sizes of augments 15 enables the achievement of a constant anterior/posterior box dimension 20 across at least two sizes of implants through the use of a limited set of augments. With a wider set of augments, it is possible to extend that constant anterior/posterior box dimension across more than two sizes of implants. Thus, with the correct size of implants, it is possible to adjust a larger implant to fit on a bone which has been resected down to that which would normally fit a significantly smaller implant. For example, correct anatomical structure may require a large implant 12 whereas disease may require resection of the distal femur to that corresponding to smaller implant 10. Rather than using smaller implant 10 which would not provide a proper knee dimension for the patient, the correct anatomically sized implant 12 may be used by adding an augment to fill the posterior space. Since the intramedullary shaft/anterior flange dimension is constant for all sizes of implants, no adjustment at the anterior end of the box 20 is necessary and the fitting of an anatomically correct implant is simplified. In addition, this system permits the desired size implant to be used on a smaller size bone yet obtain a greater degree of bone contact with the implant. Such bone contact is important for secure bonding of implants to the femur by bone ingrowth or bone cement and reduces the necessity for large volumes of bone cement or complicated bone grafts to fill in the area between the resected bone and the larger size implant.

Normally, however, the adjustment for fit will be between sequential sizes of implants, as shown in FIG. 3, with the anterior/posterior box 20 dimensions being obtained with thick or thin posterior augments. Thus, in a similar fashion to that illustrated in FIG. 3, implant 10 with a thin posterior augment will have the same anterior/posterior box dimension as implant 11 with a thick augment. Likewise, implant 11 with a thin augment will have the same A/P box dimension as implant 12 with a thick augment. In addition, implants 10, 11 and 12 are preferably sized such that placement of a thin posterior augment therein will provide the same anterior/posterior box dimension as the next smaller implant without an augment. This relationship is shown in the chart of FIG. 4 wherein the augments are listed by their thick or thin posterior options in combination with the three distal options designated 1, 2 and 3, while the four possible posterior cuts are represented by the letters A, B, C and D. The distal thickness options are provided to accommodate resection of the distal surface of the femur and correspond to the standard cuts made so that the space between the femur and tibia at full flexion and extension match, thereby promoting proper patellar tracking on the femoral component and stable collateral ligaments.

As the chart clearly shows, the present system allows more than one femoral implant size to be used to properly fit a given femur after standard cuts are made to the femoral surface. This is possible because of the standardization of construction and geometry for all the implants in the system. Furthermore, the revision procedure is simplified because the surgeon can make the cuts to the femoral surface on the basis of the system's standards with the said of pre-set cutting guides following the determination of the correct anatomical knee size.

Thus, for example, if standard cut B is made on the posterior femur, the surgeon will have a choice of implant component sizes 2 or 3, these size designations being arbitrary, to achieve a correct soft tissue balance; a thin or thick posterior augment being selected for the corresponding adjustment of the flexion gap. The chart of FIG. 4 illustrates the relationships for sequential sizes of implants. Additional sizes of posterior augments would permit such relationships between multiple sizes of implants. For example, an extra thick augment might be used to fit a size 4 implant onto a femur which has been resected down to a size 2 using cut B.

It is conceivable that there could be instances where disease or wear would affect the anterior condylar surfaces of the femur. In such instances anterior augments would be necessary. Such augments and their relationship to the implants and the distal augment thicknesses are shown in FIGS. 6, 7 and 8. The anterior augment 22 would be used to make up the bone removed from the anterior condyle and would also be based on a standardized series of cuts establishing set angles for the bone contacting surface 23 of the augments. The implant contacting surface 24 will be constant. For each angle offered, the set of augments 22 will include three sizes, arbitrarily designated E, F and G, determined by the base thickness dimension 25 which will be dependent on the distal augment thickness as shown in the chart in FIG. 8. Thus, when an anterior augment 22 is needed and a distal augment of thickness 1 has been used, anterior augment E will be selected; with distal thickness 2, anterior augment F; and with distal augment thickness 3, anterior augment G. Preferably, the angle of surface 23 is 15° from vertical. When other angles are to be offered a separate series of augments corresponding to that angle will be needed.

Inasmuch as the implant of this invention is based around the intramedullary stem as a constant point of reference, the surgical procedure involves first reaming the intramedullary canal of the femur. In this manner, all the subsequent resection cuts may be made using the intramedullary canal as a reference, any guide means being used having a support shaft which fits in the intramedullary canal or being attachable to the reamer used to prepare the canal. The guides, and the resection cuts produced therewith, will have constant angular characteristics relative to the reference point and corresponding to the geometric constants of the set of implant components.

Although designed primarily for use in revision surgery and replacement of a previously implanted femoral component, the apparatus of this invention is also applicable to an initial reconstruction procedure as a first implant. In such a case, the initial resection of the femur would be performed using the intramedullary canal as the reference point and the standardized construction of the implant components of the system as the guide for such resection. As in a revision process, the correct size implant would be selected based on the anatomical characteristics of the knee. This would then dictate the cuts to be made to the distal femur in order to obtain a correct fit with both the bone and the soft tissues.

Using the prosthesis of the present system in this manner will also establish the procedure for a subsequent revision using the same system. Bearing in mind the expected life of prosthetic joint implants, a subsequent revision is a likely prospect. If the implants of the present system are used in the initial procedure then the reference points and standards will already be set for the revision. The process would then involve removal of the initial prosthesis, further resection of the distal and posterior surfaces, if necessary, using the intramedullary canal as the reference point and the predetermined cuts associated with the system, selection of the augments to go with the cuts made and the size component to be used followed by implantation of the component. This can all be accomplished in a single surgical procedure in less time and without complicated custom manufacturing, trial and error fitting, bone grafts or excessive bone cement.

The foregoing description sets forth the preferred form of the apparatus of this invention and the method for its use. However, other modifications and variations will become apparent to those having skill in the art from an examination of that description and the accompanying drawings. Therefore, other variations of the present invention may be made which fall within the scope of the appended claims even though such variations were not specifically discussed.

What is claimed is:

1. In a system for human knee replacement comprising a set of implants having a plurality of progressively increasing sizes of femoral prosthesis components, each component comprising an anterior flange, first and second posterior condylar flanges, a distal condylar joint surface uniting said anterior and posterior flanges, distal femur contacting surfaces on each of said flanges and said distal condylar joint surface forming an anterior/posterior box having a size corresponding to that of the particular femoral component, and an elongated intramedullary shaft extending from the femur contacting surface of said distal condylar joint surface; and improvement comprising providing each size of said femoral components in said set with an anterior/posterior box dimension corresponding to the size of the particular femoral component whereby said anterior/posterior box dimension progressively increases with each of said progressively increasing sizes of said components, and providing each size of said femoral components in said set with a constant relationship between said anterior flange and said intramedullary shaft whereby an angle between a longitudinal axis of said shaft and said femure contacting surface of said anterior flange is identical for each size of femoral prosthesis component in said set regardless of said anterior/posterior box dimension.

2. The system of claim 1 wherein said relationship between said intramedullary shaft and said anterior flange is constant for every size of femoral prosthesis component in said set and is measured about a point corresponding to an intersection of planes defined by said femure contacting surfaces of said anterior flange and said distal condylar joint surface.

3. The system of claim 2 further comprising a series of augments attachable to said distal femure contacting surfaces of said femoral prosthesis components, said augments comprising a distal portion having a thickness dimension and a posterior portion having a thickness dimension.

4. A set of removal revision prosthesis components of progressively increasing size of implantation to a resected distal femure in knee revision surgery, each component comprising first and second posterior condylar flanges, an anterior flange, a distal conylar joint surface uniting said anterior and posterior condylar flanges, said flanges and said distal condylar joint surface having femur contacting surfaces forming an anterior/posterior box into which the reselected distal end of the femur is received said anterior/posterior box having a dimension specific to the particular component of said set, said dimension being progressively increasing with said progressively increasing sizes of said femoral components, each component further comprising an elongated intramedullary shaft extending outward from said femure contacting surface of said distal condylar joint surface for insertion into an intramedullary space of said resected femur, wherein each component in said set has an identical relationship between said anterior flange and said intramedullary shaft said relationship comprising an identical distance between the joint surface of said anterior flange and a longitudinal axis of said shaft for each size component in said set regardless of said anterior/posterior box dimension.

5. The set of femoral revision prosthesis components as in clam 4, wherein said set comprises at least two components of increasing anatomical size corresponding to knee sizes which are based on statistical averages of anatomical knee sizes for the human population.

6. The set of femoral revision prosthesis components as in claim 5, wherein said identical relationship in each size component in said set comprises an identical angel between said anterior flange and said longitudinal axis of said intramedullary shaft taken along said interior/posterior axes of said components.

7. The set of femoral revision prosthesis components as in claim 6, wherein said relationship between said anterior flange and said intramedullary shaft is identical for each component in said set and is measured about a point corresponding to an intersection of planes defined by said femure contacting surfaces of said anterior flange and said distal condylar joint surface.

8. The set of femoral revision prosthesis components as in claim 7 further comprising a set of augments having a distal portion and a posterior portion and sized to fit in said anterior/posterior box of said components, said augment portions having a thickness dimension and being provided in a set comprising individual augments having one of two posterior thickness dimensions and one of three distal thickness dimensions.

9. The set of femoral revision prostheses components as in claim 8 wherein said augments are sized such that sequential sizes of said femoral components are provided with an identical anterior/posterior box dimension by the application of said augments having appropriate posterior thickness dimensions.

10. The set of femoral revision prosthesis components as in claim 9 wherein a femoral component of one size having an augment with a thick posterior dimension installed has an anterior/posterior box dimension identical to that of the next lower size component having an augment with a thin posterior dimension.

11. The set of femoral revision prosthesis components as in claim 8 wherein said two posterior thickness dimensions and said three distal thickness dimensions correspond to resection cuts made to the distal femur.

12. The set of femoral revision prosthesis components as in claim 8 wherein said augments comprise separate distal and posterior elements.

13. The set of femoral revision prosthesis components as in claim 9 wherein said components are sized such that a component of one size having an augment with a thin posterior dimension will have an anterior/posterior box dimension identical to that of a next lower size component absent an augment.

14. The set of femoral revision prosthesis components as in claim 7 further comprising a set of augments having posterior dimensions sized to fit in said anterior/posterior box of said femoral components, said augments cooperating with said femoral components to adjust said anterior/posterior box dimension of a lager size component to a size equivalent to an anterior/posterior box dimension of a smaller size component.

15. The set of femoral revision prosthesis components as in claim 8 further comprising a set of augments for application to said anterior flange femur contacting surface, said augments having an angular relationship relative to said anterior flange.

* * * * *